United States Patent [19]

Denzel et al.

[11] 4,066,644
[45] Jan. 3, 1978

[54] PYRAZOLO [1,5-A]PYRIDO[3,2-E]PYRIMIDINE-7-CARBOXYLIC ACID HETEROCYCLIC DERIVATIVES

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 764,676

[22] Filed: Feb. 2, 1977

Related U.S. Application Data

[62] Division of Ser. No. 630,120, Nov. 7, 1975, Pat. No. 4,026,893.

[51] Int. Cl.² ............... C07D 401/14; A61K 31/415; C07D 403/14
[52] U.S. Cl. ........................ 260/256.4 F; 424/251
[58] Field of Search ..................... 260/256.4 F

[56] References Cited

U.S. PATENT DOCUMENTS 3,313,815  4/1967  Wolfe et al. ............... 260/256.4 F
3,329,679  7/1967  Sulkowski et al. ............ 260/256.4 F

OTHER PUBLICATIONS

Checchi, "Chemical Abstracts," vol. 53, 1959.

*Primary Examiner*—Paul M. Coughlan, Jr.
*Assistant Examiner*—James H. Turnipseed
*Attorney, Agent, or Firm*—Lawrence S. Levinson; Merle J. Smith

[57] ABSTRACT

New derivatives of pyrazolo[1,5-a]pyrido[3,2-e]-pyrimidine-7-carboxylic acid have the general formula

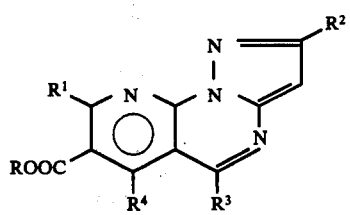

The new compounds are useful as central nervous system depressants and as anti-inflammatory agents.

10 Claims, No Drawings

PYRAZOLO[1,5-A]PYRIDO[3,2-E]PYRIMIDINE-7-CARBOXYLIC ACID HETEROCYCLIC DERIVATIVES

This application is a division of application Ser. No. 630,120, filed Nov. 7, 1975 now Pat. No. 4,026,893.

SUMMARY OF THE INVENTION

This invention relates to new derivatives of pyrazolo[1,5-a]pyrido[3,2-e]pyrimidine-7carboxylic acids and salts thereof. These new compounds have the general formula

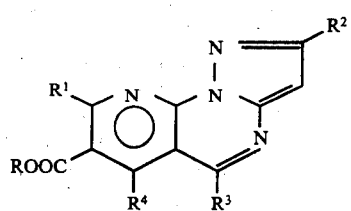

The symbols have the following meanings in formula I and throughout this specification:

R, $R^1$ and $R^3$ each is hydrogen or lower alkyl;
$R^2$ is hydrogen, lower alkyl or phenyl;
$R^4$ is hydroxy, halogen, lower alkoxy, di-lower alkylamino-lower alkoxy or a basic acyclic or cyclic amino group

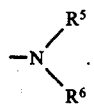

DETAILED DESCRIPTION OF THE INVENTION

The lower alkyl groups are straight or branched chain hydrocarbon groups having up to seven carbon atoms in the chain, e.g., methyl, ethyl, propyl, isopropyl, butyl, isobutyl, t-butyl, amyl, hexyl, heptyl, etc. The $C_1$-$C_4$ lower alkyl groups and especially $C_1$-$C_2$ groups are preferred.

The lower alkoxy groups are similar, including lower alkyl groups of the kind described above attached to the oxygen. The $C_1$-$C_4$ and $C_1$-$C_2$ groups similarly constitute preferred and especially preferred groups, respectively.

The halogens are the four common halogens, but chlorine and bromine are preferred especially the first.

The basic amino group

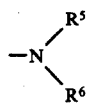

is an acyclic amino group in which $R^5$ and $R^6$ each is hydrogen, lower alkyl, phenyl, substituted phenyl (wherein the phenyl substituent is one or two halogen or trifluoromethyl groups, preferably only one), phenyl-lower alkylene or di-lower alkylamino-lower alkylene (the lower alkyl and lower alkylene groups being similar to the lower alkyl groups described above, with the $C_1$-$C_4$ and $C_1$-$C_2$ groups constituting preferred and especially preferred members, respectively). Preferably only one of $R^5$ or $R^6$ is phenyl, substituted phenyl, phenyl-lower alkylene or di-lower alkylamino-lower alkylene, the other being hydrogen. Such acyclic amino groups include, for example, amino, lower alkylamino (e.g., methylamino, ethylamino, propylamino, isopropylamino, etc.), di-lower alkylamino (e.g., dimethylamino, diethylamino, dipropylamino, methylethylamino, etc.), anilino, (o-trifluoromethyl)anilino, o-chlorophenylamino, p-bromophenylamino, benzylamino, phenethylamino, dimethylaminomethylamino, dimethylaminoethylamino, (methylethyl)aminomethylamino, dipropylaminoethylamino, etc.

The di-lower alkylamino-lower alkoxy groups represented by $R^4$ are similar to the groups referred to in the preceding sentence except for the linking oxygen in place of the nitrogen. Such groups having up to four carbons in each alkyl group are preferred. Examples include dimethylaminomethoxy, diethylaminomethoxy, diethylaminoethoxy, dimethylaminopropoxy and the like.

The basic amino group

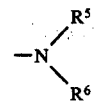

also represents a heterocyclic radical wherein $R^5$ and $R^6$ join to complete one of the groups aziridinyl, pyrrolidino, piperidino, pyrazolyl or piperazinyl. The heterocyclic (preferably piperidino and piperazinyl) can also bear as a substituent a hydroxy-lower alkyl group or one or two lower alkyl groups (preferably in a para-position, e.g., 4-methylpiperazinyl, 4-hydroxyethylpiperazinyl, 4-methylpiperidino).

The products of the examples (especially Examples 1 to 9) are preferred embodiments.

Especially preferred compounds of Formula I are those wherein

R is ethyl;
$R^1$ is hydrogen or methyl, especially hydrogen;
$R^2$ is hydrogen or lower alkyl, especially methyl;
$R^3$ is hydrogen or lower alkyl, especially methyl;
$R^4$ is lower alkylamino, especially n-butylamino or sec. butylamino.

The compounds of formula I are produced from a 7-aminopyrazolo[1,5-a]pyrimidine of the formula

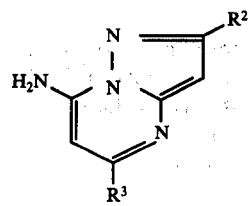

[produced analogous to the procedure described in J. Het. Chem. 11, 423 (1974)] which is made to react with an alkoxymethylenemalonic acid ester of the formula

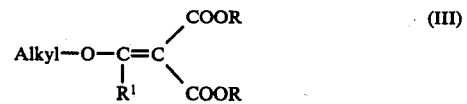

by heating at a temperature of about 140° C. The resulting compound of the formula

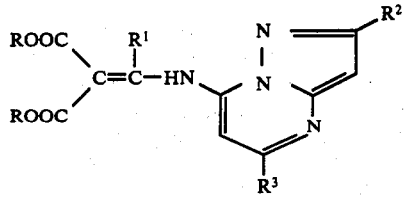

is cyclized in an inert organic solvent like diphenylether at about 230°–260° C., while distilling off the alcohol formed producing a compound of the formula

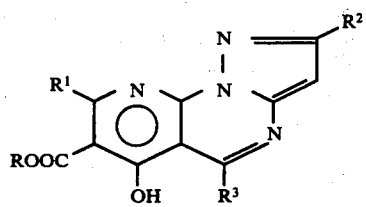

Compounds of the formula

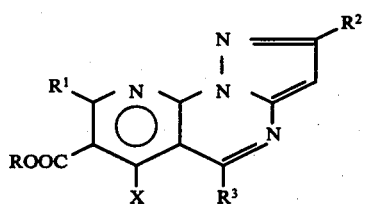

wherein X is halogen (preferably chlorine or bromine) are new intermediates, produced by reacting a compound of formula Ia with an appropriate acid halide, like phosphorus oxychloride or bromide.

Compounds of the formula

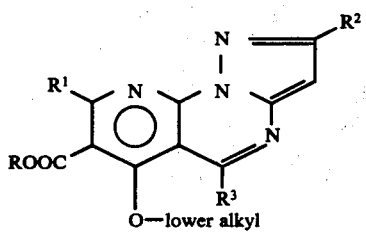

with a lower alkoxy group in the 6-position are now obtained by reaction of a compound of formula Ib with an alkali metal alcoholate, like sodium methoxide, potassium ethoxide or the like.

Compounds of the formula

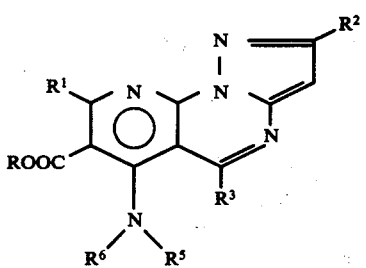

are obtained by reacting a compound of formula Ic or Ib with the appropriate amine of the formula

at elevated temperatures. Sometimes it is advantageous to use an autoclave.

The new compounds of formula I form salts which are also part of this invention. The salts include acid addition salts, particularly the non-toxic, physiologically acceptable members. These salts are formed by reaction with one or more equivalents of any of a variety of inorganic and organic acids, especially the strong acids, providing acid addition salts including, for example, hydrohalides (especially hydrochloride and hydrobromide), sulfate, nitrate, borate, phosphate, oxalate, tartrate, maleate, citrate, acetate, ascorbate, succinate or aryl- or alkanesulfonates like benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Certain members, i.e., wherein R is hydrogen, form salts with metals, e.g., alkali metals like sodium, alkaline earth metals like calcium and magnesium, etc. These salts are useful to form soluble derivatives or as intermediates. They are also within the scope of the invention.

Additional experimental details are found in the examples.

The new compounds of this invention are psychotropic agents having central nervous depressant activity and can be used as ataractic agents for the relief of anxiety and tension states, for example, in mice, cats, rats, dogs and other mammalian species. For this purpose a compound or mixture of compounds of formula I, or non-toxic, physiologically acceptable salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 5 to 15 mg. per kilogram per day, is appropriate.

The new compounds of this invention also have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the carageenan edema assay in rats or delayed hypersensitivity skin reaction test.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I or physiologically acceptable salt (preferably acid addition salt) is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion, ointment, or cream containing about 0.1 to 3 percent by weight of a compound of formula I or its salt is formulated.

The following examples are illustrative of the invention and constitute preferred embodiments. They also serve as models for the preparation of other members of the group which can be produced by suitable substitution of starting materials. All temperatures are in degrees celsius.

EXAMPLE 1

2,5-Dimethyl-6-(4-methyl-1-piperazinyl)pyrazolo[1,5-a]pyrido-[3,2-e]pyrimidine-7-carboxylic acid, ethyl ester a.

[[(2,5-dimethylpyrazolo[1,5-a]pyrimidin-7-yl)amino]-methylene]propanedioic acid, ethyl ester 168 g. of 2,5-dimethylpyrazolo[1,5-a]pyrimidin-7-amine (1 mol.) and 216 g. of ethoxymethylenemalonic acid diethyl ester (1 mol.) are heated together with stirring at 140° until the theoretical amount of alcohol has been distilled off (about 1 hour). The mixture is cooled to room temperature and the product [[(2,5-dimethylpyrazolo-[1,5-a]pyrimidin-7-yl)amino]methylene]propanedioic acid, ethyl ester is recrystallized from ethyl acetate, yield 280 g. (84%), m.p. 130°–132°.

b.

6-hydroxy-2,5-dimethylpyrazolo[1,5-a]pyrido[3,2-e]-pyrimidine-7-carboxylic acid, ethyl ester 33.2 g. of [[(2,5-dimethylpyrazolo[1,5-a]pyrimidin-7-yl)amino]methylene]propanedioic acid, ethyl ester (0.1 mol.) are heated in 100 ml. of diphenyl ether at 240° for 7 minutes. The mixture is cooled rapidly and 100 ml. of diethyl ether are added. The product, 6-hydroxy-2,5-dimethylpyrazolo[1,5-a]pyrido[3,2-e]pyrimidine-7-carboxylic acid, ethyl ester, precipitates and is filtered off, yield 20.1 g. (75%), m.p. 207°–208° (methanol).

c.

6-chloro-2,5-dimethylpyrazolo[1,5-a]pyrido[3,2-e]pyrimidine-7-carboxylic acid, ethyl ester 13.4 g. of 6-hydroxy-2,5-dimethylpyrazolo[1,5-a]pyrido[3,2-e]pyrimidine-7-carboxylic acid, ethyl ester (0.05 mol.) and 100 ml. of phosphorous oxychloride are refluxed with stirring for 5 hours. The excess of chlorinating agent is distilled off and the dark residue is poured into ice-water. 6-Chloro-2,5-dimethylpyrazolo[1,5-a]pyrido[3,2-e]pyrimidine7-carboxylic acid, ethyl ester precipitates, yield 6.4 g. (42%), m.p. 143°–145° (ethyl acetate). d. 2,5-dimethyl-6-(4-methyl-1-piperazinyl)pyrazolo1,5-a]-pyrido[3,2-e]pyrimidine-7-carboxylic acid, ethyl ester 3.04 g. of 6-chloro-2,5-dimethylpyrazolo[1,5-a]pyrido[3,2-e]pyrimidine-7-carboxylic acid, ethyl ester (0.01 mol.) and 10 ml. of N-methylpiperazine are heated at reflux temperature for 5 minutes. The excess N-methyl piperazine is removed in vacuo and the residue is treated with water. The product, 2,5-dimethyl-6-(4-methyl-1-piperazinyl)pyrazolo[1,5-a]pyrido[3,2-e]pyrimidine-7-carboxylic acid, ethyl ester, crystallizes and is filtered off, yield 3.1 g. (85%), m.p. 158°–159°.

EXAMPLE 2

6-Hydroxy-5-methylpyrazolo[1,5-a]pyrido[3,2-e]pyrimidine-7-carboxylic acid, ethyl ester a.

[[(5-methylpyrazolo[1,5-a]pyrimidin-7-yl)amino]methylene]propanedioic acid, ethyl ester By substituting 5-methylpyrazolo[1,5-a]pyrimidin-7-amine for the 2,5-dimethylpyrazolo[1,5-a]pyrimidin-7-amine in the procedure of Example 1a, 5-methylpyrazolo[1,5-a]-pyrimidin-7-yl)amino]methylene]-propanedioic acid, ethyl ester is obtained, yield 80%, m.p. 98°–100° (methanol).

b.

[[6-hydroxy-5-methylpyrazolo[1,5-a]pyrido]3,2-e]pyrimidine-7-carboxylic acid, ethyl ester By substituting the product of part a for the [[(2,5-dimethylpyrazolo[1,5-a]pyrimidin-7-yl)amino]methylene]-propanedioic acid ethyl ester in the procedure of Example 1b, 6-hydroxy-5-methylpyrazolo[1,5-a]pyrido[3,2-e]pyrimidine-7-carboxylic acid, ethyl ester is obtained, yield 73%, m.p. 190°–192° (methanol).

EXAMPLE 3

2,5-Dimethyl-6-(1-piperidinyl)pyrazolo[1,5-a]pyrido[3,2-e]pyrimidine-7-carboxylic acid, ethyl ester When 6-chloro-2,5-dimethylpyrazolo[1,5-a]pyrido[3,2-e]pyrimidine-7-carboxylic acid, ethyl ester of Example 1c is treated with piperidine according to the procedure of Example 1d, 2,5-dimethyl-6-(1-piperidinyl)-pyrazole[1,5-a]pyrido[3,2-e]pyrimidine-7-carboxylic acid, ethyl ester is obtained, yield 88%, m.p. 161°–163° (ethyl acetate).

EXAMPLE 4

6-[[3-(Dimethylamino)propyl]amino]amino]-2,5-dimethylpyrazolo-[1,5-a]pyrido[3,2-e]pyrimidine-7-carboxylic acid, ethyl ester When 6-chloro-2,5-dimethylpyrazolo[1,5-a]pyrido-[3,2-e]pyrimidine-7-carboxylic acid, ethyl ester of Example 1c is treated with (3-dimethylamino)propylamine, 6-[[3-(dimethylamino)propyl]amino]-2,5-dimethylpyrazolo[1,5-a]pyrido[3,2-e]pyrimidine-7-carboxylic acid, ethyl ester is obtained, yield 76%, m.p. 73°–75° (ethyl acetate).

EXAMPLE 5

2,5-Dimethyl-6-[(1-methylpropyl)amino]pyrazolo[1,5-a]-pyrido[3,2-e]pyrimidine-7-carboxylic acid, ethyl ester 3.0 g. of 6-chloro-2,5-dimethylpyrazolo[1,5-a]-pyrido[3,2-e]pyrimidine-7-carboxylic acid, ethyl ester of Example 1c (0.01 mol.) are dissolved in 20 ml. of alcohol. 2.1 g. of sec. butylamine (0.03 mol.) are added and the mixture is refluxed with stirring for 1 hour. The solvent and excess amine is removed in vacuo and the crystalline residue is treated with water and filtered off to obtain 2,5-dimethyl-6-[(1-methylpropyl)amino]-pyrazolo[1,5-a]pyrido[3,2-e]pyrimidine-7-carboxylic acid, ethyl ester, yield 3.1 g. (91%), m.p. 113°–115° (ethyl acetate).

EXAMPLE 6

6-(n-Butylamino)-2,5-dimethylpyrazolo[1,5-a]pyrido[3,2-e]-pyrimidine-7-carboxylic acid, ethyl ester By substituting n-butylamine for the sec. butylamine in the procedure of Example 5, 6-(n-butylamino)-2,5-dimethylpyrazolo[1,5-a]pyrido[3,2-e]pyrimidine-7-carboxylic acid, ethyl ester is obtained, yield 89%, m.p. 114°–116° (ethyl acetate).

By treating this product with a slight excess of dry ethanolic potassium hydroxide and refluxing for 3 hours under argon, the potassium salt is obtained. The addition of dilute hydrochloric acid and evaporation of the solvent yields the free carboxylic acid.

EXAMPLE 7

2,5-Dimethyl-6-(methylamino)pyrazolo[1,5-a]pyrido[3,2-e]-pyrimidine-7-carboxylic acid, ethyl ester By substituting methylamine for the sec. butylamine in the procedure of Example 5, 2,5-dimethyl-6-(methylamino)pyrazolo[1,5-a]pyrido[3,2-e]pyrimidine-7-carboxylic acid, ethyl ester is obtained, yield 78%, m.p. 208°–210° (methanol).

EXAMPLE 8

2,5-Dimethyl-6-(3-methyl)butoxypyrazolo[1,5-a]pyrido[3,2-e]-pyrimidine-7-carboxylic acid, ethyl ester 0.97 g. of 3-methyl-1-butanol (0.011 mol.) are dissolved in 50 ml. of dry benzene. After addition of 0.27 g. of sodium hydride, the mixture is refluxed for 5 hours. After this time, 3.0 g. of 6-chloro-2,5-dimethylpyrazolo[1,5-a]pyrido[3,2-e]pyrimidine-7-carboxylic acid, ethyl ester are added and heating is continued for 3 hours. The solvent is removed in vacuo, the residue is treated with dilute 10% acetic acid and extracted twice with 50 ml. portions of ether. The ether layers are combined, washed with sodium carbonate and then with water, and dried over sodium sulfate. The solution is filtered and evaporated to dryness. The residue is recrystallized from ligroin, yield 1.1 g. (31%), m.p. 75°–77°.

EXAMPLE 9

2,5-Dimethyl-6-(3-dimethylamino)propoxypyrazolo[1,5-a]pyrido-[3,2-e]pyrimidine-7-carboxylic acid, ethyl ester By substituting (3-dimethylamino)propan-1-ol for the 3-methyl-1-butanol in the procedure of Example 8, 2,5-dimethyl-6-(3-dimethylamino)propoxypyrazolo[1,5-a]-pyrido[3,2-e]pyrimidine-7-carboxylic acid, ethyl ester is obtained, yield 18%, m.p. 43°–45° (ligroin).

EXAMPLE 10

6-Chloro-5-methylpyrazolo[1,5-a]pyrido[3,2-e]pyrimidine-7-carboxylic acid, ethyl ester By substituting the product of Example 2 for the 6-hydroxy-2,5-dimethylpyrazolo[1,5-a]pyrido[3,2-e]pyrimidine-7-carboxylic acid in the procedure of Example 1c, 6-chloro-5-methylpyrazolo[1,5-a]pyrido[3,2-e]pyrimidine-7-carboxylic acid, ethyl ester is obtained.

EXAMPLE 11

6-Amino-5-methylpyrazolo[1,5-a]pyrido[3,2-e]pyrimidine-7-carboxylic acid, ethyl ester By treating the product of Example 10 with ammonia according to the procedure of Example 5, 6-amino-5-methyl-pyrazolo[1,5-a]pyrido[3,2-e]pyrimidine-7-carboxylic acid, ethyl ester is obtained. Treatment of this product with ethanolic hydrochloric acid yields the hydrochloride salt.

The following additional products are produced by the procedure of Example 1 by substituting the reactant with the desired substituent in part a, c, or d and the procedure of Example 8 for compounds wherein $R_4$ has a lower alkoxy chain or Example 6 for the free carboxylic acid or salt:

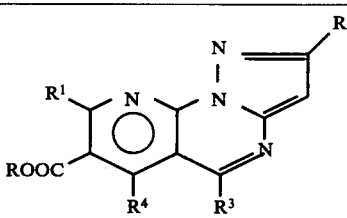

| Ex. | R | $R^1$ | $R^2$ | $R^3$ | $R^4$ |
|---|---|---|---|---|---|
| 12 | $CH_3$ | $C_2H_5$ | H | $CH_3$ | —$N(C_2H_5)_2$ |
| 13 | H | $CH_3$ | H | H | —$NHC_2H_5$ |
| 14 | $C_2H_5$ | $CH_3$ | $CH_3$ | $CH_3$ | —NHbutyl |
| 15 | $C_2H_5$ | H | 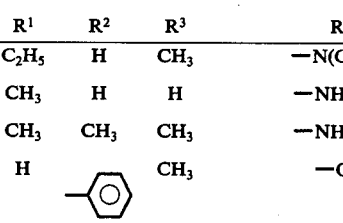 | $CH_3$ | —OH |
| 16 | $C_2H_5$ | H | 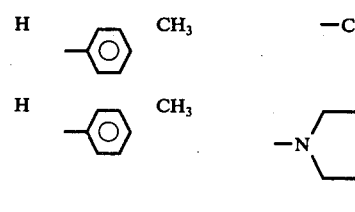 | $CH_3$ | —Cl |
| 17 | $C_2H_5$ | H | 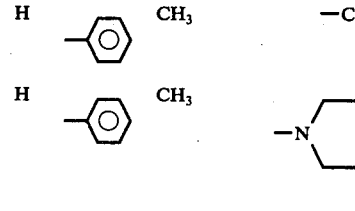 | $CH_3$ | 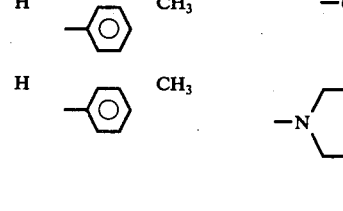 |

-continued

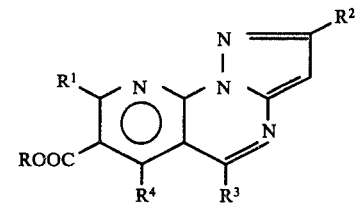

| Ex. | R | R¹ | R² | R³ | R⁴ |
|---|---|---|---|---|---|
| 18 | $C_3H_7$ | H | H | $CH_3$ | $-N(CH_3)_2$ |
| 19 | $C_2H_5$ | $C_3H_7$ | H | H | $-NH_2$ |
| 20 | $CH_3$ | H | H | $CH_3$ | -N(aziridinyl) |
| 21 | $C_2H_5$ | H | $CH_3$ | $CH_3$ | -N(pyrrolidino) |
| 22 | $C_2H_5$ | $CH_3$ | H | $CH_3$ | -N(pyrazolyl) |
| 23 | $CH_3$ | H | $CH_3$ | $CH_3$ | $-N$(piperazinyl)$N-CH_2CH_2OH$ |
| 24 | $C_2H_5$ | H | H | $CH_3$ | -N(piperidinyl)-$C_2H_5$ |
| 25 | $C_2H_5$ | H | H | $CH_3$ | $-OCH_3$ |
| 26 | $CH_3$ | H | H | $CH_3$ | $-NH-C_6H_5$ |
| 27 | $C_4H_9$ | $CH_3$ | $CH_3$ | H | $-NH-C_6H_4-CF_3$ |
| 28 | $C_2H_5$ | H | H | H | $-NH-C_6H_3Cl_2$ |
| 29 | $C_2H_5$ | H | $CH_3$ | $CH_3$ | $-NH-C_6H_4-Br$ |
| 30 | $C_2H_5$ | H | H | $CH_3$ | $-NHCH_2N(CH_3)_2$ |
| 31 | $CH_3$ | H | $C_6H_5$ | $CH_3$ | $-NHCH_2CH_2N(C_2H_5)_2$ |
| 32 | $C_2H_5$ | H | $C_6H_5$ | H | $-NH_2$ |
| 33 | H | H | $C_6H_5$ | $CH_3$ | $-NHC_4H_9$ |
| 34 | H | H | $CH_3$ | $CH_3$ | Br |
| 35 | $C_2H_5$ | H | H | $CH_3$ | $-N(CH_3)_2$ (aziridinyl dimethyl) |
| 36 | $C_2H_5$ | H | $CH_3$ | $CH_3$ | $-NHCH_2-C_6H_5$ |
| 37 | $C_2H_5$ | H | H | $CH_3$ | $-NHCH_2CH_2-C_6H_5$ |
| 38 | H | $CH_3$ | H | $CH_3$ | $-OCH_2CH_2N(C_2H_5)_2$ |
| 39 | $CH_3$ | H | H | H | $-OCH_2N(CH_3)_2$ |
| 40 | $C_2H_5$ | H | $C_6H_5$ | $CH_3$ | $-OCH_2CH_2CH_2N(CH_3)_2$ |
| 41 | $C_2H_5$ | H | $CH_3$ | $CH_3$ | $-OCH_2CH_2CH_2N(C_3H_7)_2$ |
| 42 | $C_3H_7$ | $C_2H_5$ | H | $C_2H_5$ | $-OCH_2CH_2N(CH_3)_2$ |

What is claimed is:

1. A compound of the formula wherein
R, R¹ and R³ each is hydrogen or lower alkyl;
R² is hydrogen, lower alkyl or phenyl;
R⁴ is aziridinyl, pyrrolidino, piperidino, pyrazolyl or piperazinyl, said heterocyclics being unsubstituted or substituted with a hydroxy-lower alkyl group or one or two lower alkyl groups;
and physiologically acceptable salts thereof.

2. A compound as in claim 1 wherein R⁴ is aziridinyl, pyrrolidino, piperidino, pyrazolyl or piperazinyl.

3. A compound as in claim 1 wherein R⁴ is piperazinyl.

4. A compound as in claim 1 wherein R⁴ is (lower alkyl)piperazinyl.

5. A compound as in claim 1 wherein R⁴ is piperidino.

6. A compound as in claim 1 wherein R, R¹, R² and R³ each is hydrogen or lower alkyl.

7. A compound as in claim 4 wherein R, R¹, R² and R³ each is hydrogen or lower alkyl.

8. A compound as in claim 5 wherein R, R¹, R² and R³ each is hydrogen or lower alkyl.

9. A compound as in claim 1 wherein R is ethyl, R¹ is hydrogen, R² and R³ each is methyl and R⁴ is (4-methyl-1-piperazinyl).

10. A compound as in claim 5 wherein R is ethyl, R¹ is hydrogen and R² and R³ each is methyl.